(12) United States Patent
Pacifico et al.

(10) Patent No.: US 9,827,349 B1
(45) Date of Patent: *Nov. 28, 2017

(54) SETTABLE SURGICAL IMPLANTS AND THEIR PACKAGING

(71) Applicant: ABYRX, Inc., Irvington, NY (US)

(72) Inventors: John Pacifico, Greenwich, CT (US); Aniq Darr, Riverdale, NY (US); Richard L. Kronenthal, Fair Lawn, NJ (US)

(73) Assignee: Abyrx Inc., Irvington, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/553,847

(22) Filed: Nov. 25, 2014

Related U.S. Application Data

(60) Provisional application No. 61/909,140, filed on Nov. 26, 2013.

(51) Int. Cl.
 *A61L 27/26* (2006.01)
 *A61L 27/54* (2006.01)
 *A61L 27/18* (2006.01)
 *A61L 27/16* (2006.01)
 *A61L 27/12* (2006.01)

(52) U.S. Cl.
 CPC .......... *A61L 27/26* (2013.01); *A61L 27/12* (2013.01); *A61L 27/16* (2013.01); *A61L 27/18* (2013.01); *A61L 27/54* (2013.01); *A61L 2300/112* (2013.01); *A61L 2300/414* (2013.01); *A61L 2400/06* (2013.01); *A61L 2430/02* (2013.01)

(58) Field of Classification Search
 CPC .......... A61L 27/00; A61L 27/12; A61L 27/54; A61M 5/002
 See application file for complete search history.

(56) References Cited

U.S. PATENT DOCUMENTS

| | | | |
|---|---|---|---|
| 3,995,641 A | 12/1976 | Kronenthal et al. | |
| 4,581,427 A * | 4/1986 | Dunn | C09J 4/00 156/307.3 |
| 4,673,085 A * | 6/1987 | Badouard | B65D 77/2032 206/461 |
| 4,724,250 A | 2/1988 | Schubert et al. | |
| 4,829,099 A | 5/1989 | Fuller et al. | |
| 5,810,956 A | 9/1998 | Tanis et al. | |
| 6,042,261 A * | 3/2000 | Sinders | B29B 7/7447 366/181.6 |
| 6,140,452 A | 10/2000 | Felt et al. | |
| 6,306,177 B1 | 10/2001 | Felt et al. | |
| 6,533,821 B1 | 3/2003 | Lally | |
| 7,270,813 B2 | 9/2007 | Shimp et al. | |
| 7,291,345 B2 | 11/2007 | Winterbottom et al. | |
| 7,772,352 B2 | 8/2010 | Bezwada | |
| 7,955,616 B2 | 6/2011 | Kronenthal | |
| 7,964,207 B2 | 6/2011 | Deslauriers et al. | |
| 7,985,414 B2 | 7/2011 | Knaack et al. | |
| 8,002,843 B2 | 8/2011 | Knaack et al. | |
| 8,282,953 B2 | 10/2012 | Drapeau et al. | |
| 8,303,599 B2 * | 11/2012 | Hess | A61M 5/008 206/219 |
| 8,425,893 B2 | 4/2013 | Knaack et al. | |
| 8,431,147 B2 | 4/2013 | Drapeau et al. | |
| 8,475,824 B2 | 7/2013 | McKay | |
| 8,506,983 B2 | 8/2013 | Mohan et al. | |
| 8,562,293 B2 | 10/2013 | Englander | |
| 9,314,547 B2 | 4/2016 | Bezwada et al. | |
| 2002/0122685 A1 * | 9/2002 | Lee | B65D 75/368 401/118 |
| 2005/0013793 A1 | 1/2005 | Beckman et al. | |
| 2007/0191963 A1 | 8/2007 | Winterbottom et al. | |
| 2007/0224312 A1 * | 9/2007 | Aldridge | B65D 75/30 426/5 |
| 2009/0081270 A9 | 3/2009 | Moore et al. | |
| 2009/0292029 A1 | 11/2009 | Bezwada | |
| 2009/0304773 A1 | 12/2009 | Milbocker et al. | |
| 2010/0068171 A1 | 3/2010 | Guelcher et al. | |
| 2010/0112032 A1 | 5/2010 | Guelcher et al. | |
| 2010/0197855 A1 | 8/2010 | Blom | |
| 2010/0260702 A1 | 10/2010 | Bezwada | |
| 2010/0297082 A1 | 11/2010 | Guelcher et al. | |
| 2011/0236501 A1 | 9/2011 | Guelcher et al. | |
| 2011/0237704 A1 | 9/2011 | Guelcher et al. | |
| 2012/0035610 A1 | 2/2012 | Deslauriers et al. | |
| 2012/0269892 A1 | 10/2012 | Mossaad et al. | |
| 2013/0023885 A1 * | 1/2013 | Madden | A61M 5/19 606/93 |
| 2013/0236513 A1 | 9/2013 | Guelcher et al. | |
| 2014/0213688 A1 | 7/2014 | Bezwada et al. | |

FOREIGN PATENT DOCUMENTS

| | | | | |
|---|---|---|---|---|
| EP | 2036944 A1 * | 3/2009 | | C08G 18/10 |
| WO | WO-04009227 A2 | 1/2004 | | |
| WO | WO-2010/011941 A2 | 1/2010 | | |
| WO | WO-2010/011941 A3 | 1/2010 | | |
| WO | WO-13036525 A2 | 3/2013 | | |

OTHER PUBLICATIONS

"Loctite Epoxy 5 minute instant mix", Henkel technical data sheet, Jun. 1, 2010.*
International Search Report issued in International Application No. PCT/US2012/053778 dated Mar. 4, 2013.

* cited by examiner

*Primary Examiner* — Gina Justice
(74) *Attorney, Agent, or Firm* — Mintz Levin Cohn Ferris Glovsky and Popeo, P.C.; Muriel Liberto, Esq.

(57) ABSTRACT

The present invention relates to settable compositions for use in surgery. The invention also provides related compositions, including surgical kits and packages, as well as methods of making and using the settable compositions.

40 Claims, No Drawings

SETTABLE SURGICAL IMPLANTS AND THEIR PACKAGING

FIELD OF THE INVENTION

The present invention relates to the field of medical implants, particularly settable, implantable compositions for medical use in tissue hemostasis, repair and reconstruction and packaging for such compositions.

BACKGROUND

Biodegradable polymers have become increasingly important for a variety of biomedical applications including biomedical implants, such as stents, and coatings applied to those implants, tissue engineering scaffolds, and soft-tissue adhesives. Segmented polyurethane elastomers in particular have come into wide use as biomaterials due to their superior mechanical properties and chemical versatility. PCT International Application Publication No. WO 2004009227 describes certain degradable polyurethane compositions for use as tissue engineering scaffolds. U.S. Pat. No. 6,306,177 (Felt et al.) describes curable polyurethane compositions comprising a plurality of parts capable of being sterilized, stably stored, and mixed at the time of use in order to provide a flowable composition upon mixing that is sufficiently flowable to permit it to be delivered to the body by minimally invasive means. U.S. Patent Application Publication No. 20050013793 (Beckman et al.) also describes degradable polyurethanes for e.g., tissue engineering and particularly for bone repair and replacement. U.S. Pat. No. 4,829,099 (Fuller et al.) describes certain absorbable polyisocyanates for use as surgical adhesives. U.S. Pat. Nos. 8,002,843 and 7,985,414 (Knaack et al.) describe a biodegradable polyisocyante (such as lysine diisocyanate) with an optionally hydroxylated biomolecule to form a degradable polyurethane. U.S. Pat. No. 7,964,207 (Deslaurier et al.) describes osteoconductive polyurethane compositions having mechanical properties consistent for use in bone repair. For certain applications, in addition to being biodegradable, it is advantageous for a surgical implant to be moldable or formable, for example to optimize its placement at the implant site and/or to fill voids in hard or soft tissue at the site of implantation. U.S. Pat. No. 8,431,147 and U.S. Pat. No. 8,282,953 (Warsaw Orthopedic, Inc) describe malleable implants containing demineralized bone matrix. The "malleable implant compositions" described in these patents contain a particulate solid collagen material and a particulate solid DBM material along with a liquid carrier that comprises an aqueous gel of alginate. Alginate/DBM based compositions are also described in U.S. Pat. No. 8,506,983 (Warsaw Orthopedic, Inc). US 20130236513 (Guelcher et. al, Vanderbilt Univ.) describes polyurethane composites that, in some aspects, may be "processed" as a reactive liquid that subsequently cures in situ to form a solid composite.

SUMMARY OF THE INVENTION

The present invention provides compositions and methods relating to moldable surgical implants suitable for use in hard and soft tissue repair. In one embodiment, the compositions are particularly suitable for use in bone repair, as bone void fillers, bone cements, and bone hemostats. In another embodiment, the compositions are suitable for soft tissue repair, for example as soft tissue adhesives.

The compositions of the invention are provided in the form of a curable or settable composition comprising a plurality of component parts of which are packaged separately, optionally sterile, and adapted to be mixed at the time of use to initiate a curing reaction. Preferably, the component parts, once mixed, do not require a catalyst for curing. The terms "settable" and "curable" are used interchangeably herein. In one embodiment, the fully cured composition has mechanical properties suitable for drilling or accepting a surgical screw without shattering or splintering. In one embodiment, the component parts of the composition are in the form of a putty or paste which is moldable, preferably hand-moldable, and in some embodiments sufficiently flowable for extrusion, for example, from a syringe. The homogenous composition formed from the mixture of the component parts is also in the form of a putty or paste which is moldable, preferably hand-moldable, and in some embodiments sufficiently flowable for extrusion, for a period of time after mixing and during curing. In one embodiment, the period of time for complete cure into a hardened final form is from about 6 to 12 hours or from about 6 to 24 hours. In one embodiment, the fully cured composition is drillable or machineable. In one embodiment, the settable composition cures into a final form that is thermoplastic and can be softened to return it to a hand-moldable state by applying heat sufficient to warm the composition to a temperature at least higher than 40° C., preferably between 40° C. and 100° C. In accordance with this embodiment, where the composition sets or cures prematurely during use, it may be heated until it becomes moldable again for a period of time until it cools. The compositions of the invention and their component parts are preferably not in a low viscosity liquid form.

In one embodiment, the component parts each comprise an additive, such as a colorant or dye, that imparts a color to the component. In one embodiment, each component comprises a different colorant or dye such that when the component parts are combined to form the settable composition, the different colors mix to form a new color, which new color is also indicative that the composition has been mixed to homogeneity. In one embodiment, the component parts can be mixed to homogeneity within about 1 minute or less, or within about 2 minutes.

The invention also provides related compositions, including surgical kits and packages, as well as methods of making and using the settable compositions. In one embodiment, the invention provides a package comprising one or a plurality of settable compositions, each composition consisting of a set of two or more individual components, the components of a set comprising amounts of reagents which, upon mixing, react and cure into a final hardened form over a period of time, preferably at room or body temperature. Each component is physically separated from the other components of the set within the package, and optionally, from other sets of components. In one embodiment, the set consists of 2, 3, or 4 individual components. In one embodiment, the components are sterile. In one embodiment, the package is adapted to permit the removal of one set of components at a time while leaving the remaining sets in a sealed, sterile, environment. In one embodiment, the package comprises an upper peelable film configured to allow the exposure of one set of putties at a time. In one embodiment, each component is physically separated from the other components of its set within the package by means of a compartment or plurality of compartments in the package. In a further embodiment, each set of components may optionally be separated from other sets of the package by perforations allowing the set to be conveniently separated either before or after opening and removing the contents.

In one embodiment, the plurality of compartments comprises depressions or wells in a heat-sealable metal foil-based sheet. In one embodiment, the compartments of a set are flexible and separated by at least one breakable seal adapted to allow the component putties of the set to be mixed together when the seal is broken. In one embodiment, the compartments are in the form of one or more syringes, preferably one or more foil-enclosed syringes. In one embodiment, the compartments are in the form of a single syringe, preferably a foil-enclosed syringe, adapted to maintain individual component putties of a set separated from each other within the single syringe. In one embodiment, the compartments are in the form of a plurality of syringes and each syringe contains a single component of a set. In one embodiment, each compartment comprises one or more surfaces in contact with an individual component, the one or more surfaces comprising or consisting of a low surface energy material selected, for example, from the group consisting of polytetrafluoroethylene (PTFE), silicone, polypropylene, polyethylene, and polystyrene.

In one embodiment, the package further comprises an outer, heat sealable, preferably water impermeable or water resistant envelope completely surrounding the package, and a desiccant. In one embodiment, the outer envelope is a heat sealed, water impermeable or water resistant foil package.

In one embodiment, the settable composition consists of a set of components, each in the form of a putty, that, upon mixing, react and cure into a polyurethane or polyureaurethane composition. In one embodiment, at least one or at least two of the putty components of the set comprises an isocyanate component, a polyol/polyamine component, and a particulate component. In one embodiment, the particulate component is present in an amount of about 5-85 wt % based on the weight of the putty component. In one embodiment, the particulate component is selected from one or more of calcium sulfate, calcium phosphosilicate, sodium phosphate, calcium aluminate, calcium phosphate, magnesium phosphate, hydroxyapatite, phosphate glass, biomimetic carbonate apatite, biphasic calcium phosphate/hydroxyapatite, demineralized bone matrix, mineralized bone, or non-resorbable metallic or polymeric materials, such as polytetrafluoroethylene, polymethylmethacrylate, micronized titanium and powdered stainless steel.

In one embodiment, the set consists of two putties, A and B, and the isocyantate component consists of a diisocyanate which is aromatic or aliphatic. Putty A comprises 15-40% of the isocyanate component, 0.5-5% of the polyol component, and 50-75% particulate material, based upon total weight of Putty A; Putty B comprises 1-10% of the isocyanate component, 3-15% of the polyol component, and 65-95% or 75-85% particulate material, based upon total weight of Putty B. In one embodiment, the polyol in Putty A is present in a prepolymer with the isocyanate component such that there is substantially no unreacted polyol in Putty A and the isocyanate component in Putty B is present in a prepolymer such that there is substantially no unreacted isocyanate in Putty B.

In one embodiment, the set consists of two putties, A and B. Putty A comprises 15-40% of the isocyanate component, 0.5-5% of the polyol component, and 40-85% particulate material, based upon total weight of Putty A; Putty B comprises 1-10% of the isocyanate component, 3-15% of the polyol component, and 65-95% or 75-85% particulate material, based upon total weight of Putty B.

In one embodiment, the set consists of two pastes, A and B. Putty A comprises 15-40% of the isocyanate component, 0.5-5% of the polyol component, and 50-75% particulate material, based upon total weight of Putty A; Putty B comprises 1-10% of the isocyanate component, 3-15% of the polyol component, and 25-50% or 5-25% particulate material, based upon total weight of Putty B.

In one embodiment, the set consists of two pastes, A and B. Putty A comprises 15-40% of the isocyanate component, 0.5-5% of the polyol component, and 40-85% particulate material, based upon total weight of Putty A; Putty B comprises 1-10% of the isocyanate component, 3-15% of the polyol component, and 25-50% or 5-25% particulate material, based upon total weight of Putty B.

The invention also provides methods for closing a wound by applying a composition described herein to the wound in an amount sufficient to achieve wound closure.

The invention also provides methods for achieving hemostasis at a wound site by applying a composition described herein to the bleeding wound in an amount sufficient to stop the flow of blood within a period of time, as described herein.

In one embodiment, the invention provides a biocompatible settable composition consisting of a plurality of component parts which, upon mixing, react to form a cured final composition at room or body temperature over a period time, the final composition optionally being biodegradable under physiological conditions. In one embodiment, the plurality of component parts consists of two parts, A and B, part A comprising potassium dihydrogen phosphate or sodium phosphate dibasic, or optionally magnesium oxide and a calcium containing compound suspended in one or a mixture of anhydrous partially or completely water miscible suspension vehicles and B comprises a viscosity building agent selected from one or more of a sodium, calcium or aluminum phyllosilicate or montmorillonite, a water absorbing clay, a water-absorbing polyacrylic acid, gelatin, sodium carboxymethyl cellulose and hyprocellulose, and, optionally, a particulate material selected from tricalcium phosphate, hydroxyapatite, or a mixture thereof. In one embodiment, the calcium containing compound is selected from tricalcium phosphate and hydroxyapatite, or a mixture thereof. In one embodiment, component B further comprises one or more additives selected from a colorant, an antioxidant, and a therapeutic agent. In one embodiment, the therapeutic agent is selected from one or more of an anticancer agent, an antimicrobial agent, an anesthetic agent, an analgesic agent and an osteogenic agent. In one embodiment, each component of a set of two contains a different colorant selected from primary or secondary hues such that when the colored components are mixed, the colors combine to form a third color which may be used to visually indicate homogeneity of the mixture. In one embodiment, the components can be hand mixed to homogeneity in one minute, three minutes, nine minutes, or twelve minutes. In one embodiment, one or more individual components contains an alkylpyrrolidone. In one embodiment, the first component is derived from a putty-like, concentrated aqueous solution of an optionally crosslinkable polyanionic polymer and the second component derived from a putty-like concentrated solution of an optionally crosslinkable polycationic polymer. In one embodiment, about 0.1-5% graphene is added as a particulate component.

DETAILED DESCRIPTION OF THE INVENTION

The present invention relates to curable or settable compositions for use in surgery. The invention also provides related compositions, including surgical kits and packages, as well as methods of making and using the settable compositions. The terms settable and curable are used interchangeably herein. The settable compositions described herein consist of at least two component parts that are provided as individual units, each containing reagents in amounts such that when the components are combined they form a single homogenous composition that is settable and that reacts or cures into a final hardened form over a period of time. In one embodiment, the mixture cures into a final hardened composition at either room temperature or body temperature, over a period of time, and without the need to apply additional external heat in excess of the ambient heat of the room (about 24-26° C.) or the heat of the human body (about 37° C.). In one embodiment, the period of time for complete cure into a hardened final form is from about 6 to 12 hours or from about 6 to 24 hours. In one embodiment, the fully cured composition is drillable or machinable. In one embodiment, the homogenous composition is thermoplastic and can be softened to return it to a hand-moldable state by applying heat sufficient to warm the composition to a temperature at least higher than 40° C., preferably between 40° C. and 100° C. In accordance with this embodiment, where the composition sets or cures prematurely during use, it may be heated until it becomes moldable again for a period of time until it cools.

In one embodiment, the individual components are sterile.

In one embodiment, an optional chain extender, such as a diol or diamine, or a crosslinker, such as a triol, polyol, triamine, or polyamine is added to one of the component parts before combining, or to the homogenous settable composition formed from the combining of the component parts, in an amount sufficient to increase the rate of the curing reaction.

In one embodiment, the component parts of a composition described here are in the form of a putty or paste and may be combined, for example, by hand-kneading, or by extrusion, for example through a syringe, or by otherwise combining or compounding into a single homogenous composition. In one embodiment, the component parts each comprise an additive, such as a colorant or dye, such that the additives impart a different color to each component. In one embodiment, the separate additives, each of a different color, form a third new color when the components have been mixed to homogeneity, such that the new color is indicates that a single homogenous composition has been formed. In one embodiment, the component parts consist of part A and part B, part A comprises a colorant or dye which gives part A a red color, part B comprises a colorant or dye which gives part B a blue color, and a composition of a substantially purple color is formed from the combination of parts A and B to homogeneity. In one embodiment, the component parts can be mixed to homogeneity within about 1 minute or less, or within about 2 minutes.

In one embodiment, each component of a settable composition of the invention is in the form of a putty and the homogenous settable composition that results from their combination is also in the form of a putty for a period of time after initiation of the curing reaction. The term "putty" refers to a composition that is soft, moldable, preferably nonelastic, and cohesive.

In one embodiment, a putty is formed as a suspension or dispersion of particulates within a liquid. As an illustrative example of this general form, one can consider the non-medical putty composition referred to as glaziers putty, which is diatomaceous earth or clay suspended in a drying oil such as linseed oil. In one embodiment of the present invention, the liquid components are selected from liquids such as the polyol, chain extender and the polyisocyanate. Non-reactive, nontoxic organic liquids such as esters, ethers and hydrocarbons may be employed in this context. In one embodiment, the solid components are particulate materials selected from one or more of calcium phosphate, siliconized calcium phosphate, a substituted calcium phosphates where the substitution is with magnesium, strontium, or silicate, for example, calcium phosphosilicate, calcium pyrophosphate, hydroxyapatite, polyaryletherketone-based materials (Lg., PEK, PEEK, PEKK, PEEKK and PEKEKK), polyurethanes, polyureaurethanes, polymethylmethaerylate (PMMA), silicone polymers, glass-ionomer, absorbable phosphate glass, calcium sulfate, tricalcium phosphate (e.g., beta tricalcium phosphate), demineralized bone matrix (DBM), or mineralized bone, or any combination of the foregoing.

In one embodiment, the particulate component for inclusion in a component part of the compositions described here is selected from one or more of calcium sulfate, sodium phosphate, calcium aluminate, strontium phosphate, calcium strontium phosphate, tricalcium phosphate, calcium pyrophosphate, magnesium phosphate, hydroxyapatite, biomimetic carbonate apatite, biphasic calcium phosphate/hydroxyapatite, mineralized bone matrix, demineralized bone matrix, glass ionomer, absorbable phosphate glass and non-resorbable particulate metallic or polymeric materials such as stainless steel or titanium powder or nanoparticles, polyurethane, polyureaurethane, polymethacrylic acid and polyarylether ketones such as PEK, PEEK, PEKK, PEEKK and PEKEKK particles. Further examples of particulate materials are provided infra.

The particles of a particulate material used in the component parts of the compositions described here may be porous or non-porous particles. In one embodiment, the particles are porous and the degree of porosity is sufficient to permit the ingress of cells or fluids into the composition after its placement in situ. Particle size may also be varied from about 0.05 to less than or equal to 1 millimeter or 2 millimeters in diameter to control the consistency, with smaller particle sizes yielding smoother more cohesive putties.

In one embodiment, the putty consistency is formed by the inclusion of viscous prepolymers in at least one of the component parts of the composition. In this context, a prepolymer comprises reactive components that are liquids and/or powders which are partially reacted by limiting one or more of the reactants to produce more viscous versions of the liquid components. Softeners such as nonreactive surfactants, hydrophilic compounds or polymers such as polyethylene glycol dialkyl ethers, etc., may also be added.

The settable compositions described herein are biocompatible and suitable for use in vivo, particularly during surgery. The term "biocompatible" refers to materials that do not induce undesirable effects when administered or implanted in vivo, for example, an immune reaction and/or an inflammatory reaction, or other adverse reaction that is detrimental to wound healing and/or to the implant recipient. A biocompatible material may also be referred to as "non-toxic". In one aspect, the biocompatible compositions described here form from a low-exotherm reaction and their formation does not produce toxic fumes or tissue-damaging amounts of heat. In another aspect, where the compositions are biodegradable, their degradation under physiological conditions does not produce toxic by-products and/or is not toxic to the implant recipient. In one embodiment, the maximum exotherm (amount of heat i.e., temperature increase, generated by the reaction) of the polymerization reaction is 20° C. or less, most preferably 10° C. or less.

In one embodiment, the compositions are fully or partially biodegradable. The terms "degradable", "biodegradable", "resorbable", and "absorbable" are used interchangeably herein to refer to the ability of the claimed compositions to degrade (partially or completely) under physiological conditions into non-toxic products that can be metabolized or excreted from the body within a period of time, generally several days and up to a year or about 18 to 24 months or longer. In one embodiment, the composition is fully biodegradable within about 12 months. Compositions may be considered non-biodegradable if they remain stable in vivo for periods exceeding about ten years.

In one embodiment, the compositions are osteopromotive or comprise an osteopromotive component. The term "osteopromotive" encompasses the ability to support, enhance or accelerate the growth of new bone tissue by one or more of osteoconduction, and osteoinduction. In one embodiment, the compositions further comprise one or more osteopromotive recombinant proteins selected from the group consisting of bone morphogenic proteins (e.g., BMP-2, BMP-7), platelet derived growth factor, transforming growth factor beta, epidermal growth factor, NELL and UCB-1. In one embodiment, the osteopromotive component comprises an osteoconductive component. In one embodiment, the osteoconductive component comprises or consists of particles of an osteoconductive material, such as particles of tricalcium phosphate or bioglass. The term "bioglass" refers to a group of glass-ceramic materials comprising $SiO_2$, $Na_2O$, $CaOP_2O_5$, and combinations of these. Preferably, the particles are in a size range of 1 micron to 2,000 microns average mean diameter.

In certain embodiments, a homogenous settable composition as described here is also mechanically hemostatic. In one embodiment, the homogenous settable composition has the property of adhering to the surface of actively bleeding bone with sufficient strength to stop the bleeding within at least about 1 minute, at least about 2-5 minutes, or at least 5-10 minutes. In accordance with this embodiment, the homogenous settable composition remains both moldable and sufficiently adhesive to adhere to the surface of actively bleeding bone for a period of time following the combination of component parts that initiated the curing reaction. In one embodiment, the period of time is from about 1 to 30 min, about 1 to 15 min, or about 1 to 10 min. It should be understood that characterizing the adhesive properties of the settable composition during a period of time after initiation of the curing reaction in relation to bleeding bone is meant for descriptive purposes only, and not intended to limit the use of the compositions to hard tissues. In some embodiments, the settable compositions described here may also be useful as soft-tissue hemostats. In addition, although the settable compositions are described here as having physical properties suitable for mechanical (tamponade) hemostasis, in certain embodiments a hemostatic composition of the invention may also contain one or more agents that act as active chemical hemostats. Non-limiting examples include blood clot-inducing agents such as prothrombin, thrombin, oxidized cellulose, microcrystalline collagen, gelatin foam, collagen sponge, fibrinogen, and fibrin. In one embodiment, the composition may also comprise one or more of epinephrine, tannic acid, ferrous sulfate, and the double-sulfates of a trivalent metal and a univalent metal such as potassium aluminum sulfate and ammonium aluminum sulfate. Thus, a settable composition may be hemostatic, mechanically or chemically, or by a combination of mechanical and chemical hemostasis.

Surgical Kits and Packages

The invention provides a surgical kit or package comprising a settable composition described herein. As discussed above, the settable compositions described herein consist of at least two components that are provided as individual units, each containing reagents in amounts such that when the components are mixed, they react or cure into a hardened composition after a period of time, preferably at room or body temperature.

As a practical matter, during use of a settable composition in surgery, freshly made material may be required at widely spaced points in time. If the material is not mixed just before use, its moldability, uniformity, and adherence to the surfaces to which it is applied will be diminished. In this context, the adhesive nature of the material is a function of its uncured state. In some embodiments, the composition as it cures bonds to the tissue at the site of implantation, for example bone tissue. And if the material is compounded too early, it may set before it can be applied. In such a state it will be insufficiently moldable, insufficiently adhesive, and unsuitable for use.

The surgical kits and packages described herein provide a solution to this problem by providing the availability of freshly made settable material at different times during a surgical procedure.

In one embodiment, the present invention provides a container comprising two or more compartments, each compartment containing an amount of a component. Where the container comprises multiple sets of components, the compartments are adapted such that each set can be removed without disturbing the other sets in the package. If the components are sterile, the container is adapted such that each set of components can be aseptically removed without compromising the sterility of the remaining sets. For example, the separate compartments may form the lower part of a vacuum-formed container with an upper peelable film. The construction of the container allows for the removal of a single set of components from their respective compartments just before use. The components, thus exposed, then are removed from the container by a gloved finger or by using an instrument and are kneaded together until homogenous to form a single composition for surgical implantation. The composition thus formed will initially be in a moldable form. In one embodiment, the composition is in the form of a putty, and the components of each set are also in the form of putties. As the composition sets, it hardens into a solid form. When needed, the next set of compartments in the unit is exposed by peeling down their covering film and kneading the newly exposed putties together until homogeneous and ready for surgical use. In one embodiment, the container comprises pairs of compartments and the set of components is a pair. In one embodiment, the container comprises 2 to 12 sets of components.

The compartments of the package may be, for example, in the form of a depression or well, or the compartments may comprise walls made of a flexible material having any shape, or an amorphous shape. In one embodiment in which the package comprises multiple pairs of putties, the package may contain any desired number of putty pairs. In one embodiment, the package consists of 2, 4, 8, 10, or 12 putty pairs. In one embodiment, perforations may be placed between pairs to facilitate removal of a pair before or after opening.

In one embodiment the package comprises separate compartments or wells of a lower, vacuum-formed container with an upper peelable film, designed to allow a single set of putties to be removed from a single set of compartments as needed, e.g., just before use during surgery. In one embodiment, the set consists of two and a single package contains from 2 to 12 sets of putties.

In another embodiment, the package comprises a syringe component. In one embodiment, the syringe component is a single syringe pre-loaded with measured amounts of a set of putties in separate internal compartments of the syringe such that when the syringe plunger is depressed, amounts of each component are dispensed or extruded from the syringe to form a composition that will harden into a final solid (cured) form over a period of time at room temperature or body temperature. In one embodiment, the syringe component comprises two or more syringes, each pre-loaded with one component of a set. In one embodiment, the set consists of two components.

In another embodiment, the package comprises separate flexible compartments within a flexible plastic container, each compartment having a seal that, when disrupted, allows the contents of the compartments to mix together into a common flexible plastic compartment that is configured to allow mixing of the contents within the common flexible plastic compartment. In one embodiment, the package is flexible enough to allow mixing by hand-kneading. In a further embodiment, after mixing is complete, an orifice is cut into the container to allow removal of the mixed components.

In one embodiment, the package comprises or consists of a heat sealed or heat sealable foil package. In one embodiment, the package further comprises an outer envelope completely surrounding the package, and a desiccant. In one embodiment, the outer envelope is a heat sealed, pinhole free foil package.

In one embodiment, the package comprises a surface which is in contact with the components, said surface having a surface energy substantially equal to or less than the surface energy of the components, or both, such that the component does not adhere or adheres weakly to the surface. In one embodiment, the surfaces of the package that are in contact with the components are coated with a surface having a surface energy substantially equal to or less than the surface energy of the components such that they do not adhere, or adhere weakly to, the surface. In one embodiment, the surface is formed of a material selected from the group consisting of polytetrafluoroethylene (PTFE), silicone, polypropylene, polyethylene, and polystyrene.

In certain embodiments, a package has a shelf life of at least 1-2 years. In certain embodiments, the package has a shelf life of 6 months, 12 months, 18 months, 24 months, or 36 months.

The invention also provides a method for making a settable composition, the method comprising the steps of providing a package as described herein, the package containing a single set or multiple sets of components which, when mixed together, cure into a final hardened composition, and mixing a set of components into a homogenous mass. In another embodiment, the method comprises the steps of extruding measured amounts of a set from one or more syringes and kneading them together to form a single homogenous mass which cures into a final hardened composition. In one embodiment, the method comprises the steps of providing a package comprising a set of components in separate flexible compartments within a flexible container, the compartments having a breakable seal that, when broken, allows the contents of the compartment to enter into a further flexible compartment, breaking the seal such that the set of components enters into the further compartment, mixing the components into a homogenous mass within the further compartment.

As an aid to manipulating the components after extrusion from the syringe or syringes, or after removal from the packaging of the invention, the surgeon may employ a device having a pliable structure with an application surface having a surface energy substantially equal to or less than the surface energy of the composition such that the composition does not adhere or adheres very weakly to the device. The device is preferably in the form of a sheet. Suitable materials for forming the application surface include, for example, polytetrafluoroethylene (PTFE), silicone, polypropylene, polyethylene, and polystyrene. Such devices are described in US 2012/0035610.

The compositions, packages and methods of the invention are for use in surgical procedures. Preferably, the surgical procedures are practiced on humans, but they may also be used on other mammals such as a dog, a cat, a horse, a cow, a pig, or a non-human primate. In one embodiment, the surgical procedure is a procedure for the repair of cranial defects and cranioplasty applications or for repair and reconstruction of the sternum. In one embodiment, a composition as described herein is suitable for use as a tissue adhesive, a hemostat, a bone cement, or a bone void filler.

In one embodiment, a composition, as described herein, is suitable for an orthopedic application as a bone hemostat, a bone adhesive, a bone void filler, or a bone cement. The term "bone cement" is meant to distinguish related surgical implants, such as soft tissue adhesives, which may not possess the mechanical properties suitable for use in bone repair. A bone cement composition, when fully cured, has compressive strength, tensile strength, and elasticity suitable for use in bone repair or reconstruction. The solid form also bonds to bone or suitable metal surfaces and reaches a supporting bond strength within about 90 minutes and fully cures within about 24 hours. The solid form further bonds with tensile and shear strength comparable with normal bone within about 72 hours. In one embodiment, the mixture of putties fully cures into its solid form at room temperature or body temperature within about 90 minutes or about 120 minutes.

In one embodiment, the fully cured composition is suitable for use in bone repair or as a bone cement or bone void filler and has a compressive strength of from 30 to 150 MPa, or greater, a tensile strength of from 20 to 80 MPa, or greater, and an elasticity defined by a Modulus of Elasticity of from 1,400 to 1,800 MPa, or greater. In certain embodiments, the compressive strength is at least 30 MPa, at least 40 MPa, at least 50 MPa, at least 60 MPa, at least 70 MPa, at least 80 MPa, or at least 100 MPa. In some embodiments, the compressive strength is greater than 100 MPa or greater than 150 MPa. In one embodiment, the compressive strength is between 100 and 150 MPa or between 150 and 200 MPa. Preferably, the solid form is sufficiently durable to be drillable or machineable. In certain embodiments the solid form has a tensile strength of at least 20 MPa, at least 30 MPa, at least 40 MPa, at least 50 MPa, at least 60 MPa, or at least 80 MPa. In certain embodiments the solid form has a Modulus of Elasticity of at least 1,400 MPa, at least 1,500 MPa, at least 1,600 MPa, or at least 1800 MPa. In one embodiment, the solid form has a compressive strength of at least 60 or 70 MPa, a tensile strength of at least 40 or 50 MPa, and an elasticity of at least 1,600 or 1,800 MPa.

In one embodiment, the fully cured composition is suitable for use in soft tissue and has a compressive strength of from 0 to 25 MPa, from 0 to 10 MPa, or from 0 to 5 MPa, and a tensile strength of from 0.005 to 80 MPa, or from 0.005 to 20 MPa, or from 0.005 to 15 MPa. In certain embodiments, the compressive strength is less than 30 MPa, less than 25 MPa, less than 20 MPa, less than 10 MPa, or less than 5 MPa.

The mechanical properties described here refer to the properties of the composition alone, without the addition of other, optional, materials which may further increase these physical properties, especially compressive strength. In one embodiment, the compositions of the invention do not comprise an optional particulate material. In certain embodiments, the particulate material, if present, is present in an amount up to about 80% by weight of the composition.

In one embodiment, the compositions are fully or partially degradable under physiological conditions within a period of time. Where the compositions are fully degradable, they are degraded within about 12 months. The degradation may be enzymatic or non-enzymatic or a combination of both. In one embodiment, the compositions of the invention are initially degradable into non-toxic products by a non-enzymatic hydrolysis under physiological conditions. In a preferred embodiment, the compositions are fully degradable within a period of time less than 12-24 months. In certain embodiments, the polymer degradation time does not exceed 3 months or 6 months. In one embodiment, a composition of the invention is degradable within about 2 to 4 weeks after placement in vivo. In other embodiments, a composition of the invention is fully degradable within about 4 to 6 weeks, or within about 2 to 4 months, 4 to 6 months, 6 to 8 months, or 8 to 12 months. In certain embodiments, the compositions comprise components that are fully degradable or absorbable. In other embodiments, the compositions are comprised of components that are partially degradable or absorbable, or non-degradable. In certain embodiments, the compositions are formed from a combination of fully degradable, partially degradable, and/or non-degradable components.

Cyanoacrylate- and Methylidene Malonate Ester-Based Compositions

In one embodiment, the settable composition of the invention consists of at least two components that, when mixed together, form a mixture that cures into a fully hardened polymer composition comprising either methylidene malonate or alkyl cyanoacrylate esters such as octyl cyanoacrylate polymers. The first component comprises, for example, either diethylmethylidene malonate or octyl cyanoacrylate monomer, a viscosity builder such as a minor amount of poly(diethylmethylidine malonate) or poly(octylcyanoacrylate), a free radical polymerization inhibitor component, e.g., hydroquinone, an acid component to inhibit based-catalyzed polymerization, e.g., sulfur dioxide and an optional anhydrous particulate component. The one or more additional components comprise the viscosity builder of the first component and, optionally, a particulate material, and one or more additional optional additives. In one embodiment, the one or more additional optional additives are selected from a colorant, a therapeutic agent and a radiopaque agent.

The one or more additional components may further comprise an optional therapeutic agent. In one embodiment, the therapeutic agent is selected from one or more of an anti-cancer agent, an antimicrobial agent, an antibiotic, a local anesthetic or analgesic, and an anti-inflammatory agent.

In one embodiment, the one or more additional components may further comprise a bone-growth promoting agent. In one embodiment, the bone growth promoting agent is selected from bone morphogenic protein and demineralized bone matrix, and mixtures thereof. In one embodiment, the bone-growth promoting agent is an osteopromotive recombinant protein selected from the group consisting of bone morphogenic proteins, platelet derived growth factor, transforming growth factor beta, epidermal growth factor, NELL and UCB-1, and combinations thereof.

In one embodiment, the composition comprises two putty components, A and B; and putty A comprises 20-50% of the diethylmethylidene malonate or octyl cyanoacrylate monomer, 1-15% of the viscosity building component, 0-75% particulate material, based upon total weight of putty A, a radical polymerization inhibitor component and an acidic polymerization inhibitor component; putty B comprises 3-40% of the viscosity building component, and, optionally, 0-85% of particulate material, based upon the total weight of putty B, and one or more optional therapeutic agents or growth promoting agents. In one embodiment, the viscosity building component comprises polymerized monomer, the radical induced polymerization inhibitor component comprises or consists of hydroquinone and the acid induced polymerization inhibitor component comprises or consists of sulfur dioxide.

Magnesium Phosphate-Based Compositions

In one embodiment, the settable composition of the invention consists of at least two components that, when mixed together, form a mixture that cures into a fully hardened non-polymeric composition. The first comprises potassium dihydrogen phosphate, magnesium oxide, and a calcium containing compound such as, e.g., tricalcium phosphate and/or hydroxyapatite $(Ca_{10}(PO_4)_6(OH)_2$. The first component suspended in one or a mixture of anhydrous, nontoxic, partially water-miscible, inert suspension vehicles, for example one or a mixture of two or more of triacetin, a Pluronic (poloxamer) such as Pluronic L-35, and acetyl triethyl citrate, or similar liquids. A nontoxic viscosity building agent may be added, if necessary. The one or more second component comprises water, and one or a mixture of two or more viscosity building agents. In one embodiment, the viscosity building agent or agents are selected from sodium carboxymethyl cellulose, sodium alginate, Carbomer, carrageenan, aluminum silicate (Bentonite), gelatin, collagen, and chitosan. In one embodiment, the viscosity building agent is present at about 75-85 wt %. The second putty component may also optionally comprise a particulate material. In one embodiment the particulate material is selected from tricalcium phosphate and hydroxyapatite, or mixtures thereof. In one embodiment, the one or more additional second components may also optionally comprise one or more additional additives selected from a colorant, an antioxidant, and a therapeutic agent, for example, a statin.

In one embodiment, the therapeutic agent is selected from one or more of an anti-cancer agent, an antimicrobial agent, an antibiotic, a local anesthetic or analgesic, a statin and an anti-inflammatory agent. In one embodiment, the one or more additional component putties may further comprise a bone-growth promoting agent.

In one embodiment, the composition comprises two putty components, A and B, putty A comprising a methylidene malonate ester and a poly(methylidene malonate ester) in amounts ranging from 30 to 70% and putty B comprising poly(methylidenemalonate ester), in amounts ranging from 30 to 100%, wherein the amounts are based upon total weight of the composition.

In one embodiment, the composition comprises two putty components, A and B, putty A comprising or consisting of a cyanoacrylate ester in amounts ranging from 30 to 70% and a poly (cyanoacrylate) ester in amounts ranging from 70 to 30% and putty B comprising poly(cyanoacrylate) ester in amounts ranging from 97 to 100%, wherein the amounts are based upon total weight of the composition.

Isocyanate-Based Compositions

In one embodiment, the settable composition of the invention consists of at least two component parts, A and B, that when combined form a composition that cures into a fully hardened polymeric composition, the polymer selected from a polyurethane, a polyureaurethane, a polyetherurethane, or a polyesterurethane, over a period of time at body temperature (i.e., about 37 C). At least one of the component parts comprises an isocyanate component and one or both component parts comprise a polyol/polyamine component. The isocyanate component consists of an isocyanate monomer, polymer, prepolymer, or combination thereof. The isocyanate component may thus comprise one or more different isocyanates, as well as an isocyanate in both its monomeric form and its polymer or prepolymer form. The term "isocyanate" is used generically to refer to isocyanates, diisocyanates, and polyisocyanates. The term "polyol" in the context of the "polyol/polyamine component" refers to both diols and polyols. Thus, the polyol or polyamine component may comprise or consist of one or more different diols, polyols, polyamines, or mixtures of two or more diols, polyols and/or polyamines.

In one embodiment, the composition further comprises an additive selected from one or more of tocopherol esters (e.g., tocopheryl acetate), triglycerides, acetyl triethyl citrate, and fatty acid esters, to aid in handling properties and packaging. In one embodiment, the composition further comprises one or more additives selected from an antioxidant, an anhydrous particulate material, a colorant, a therapeutic agent, and a radiopaque agent. In one embodiment, the therapeutic agent is selected from one or more of an anticancer agent, an antimicrobial agent, an anesthetic agent, an analgesic agent, an anti-inflammatory agent, and an osteogenic agent.

In one embodiment, the composition further comprises an osteoconductive component. In one embodiment, the osteoconductive component also confers porosity to the composition and the porosity is sufficient to allow the ingress of fluids and/or cells (e.g., osteoclasts, blood cells) into the composition in situ. In one embodiment, the osteoconductive component comprises or consists of particles of an osteoconductive material, such as particles of tricalcium phosphate or bioglass. The term bioglass refers to a group of glass-ceramic materials comprising $SiO_2$, $Na_2O$, $CaOP_2O_5$, and combinations of these.

In one embodiment, porosity is not introduced into the composition as it cures by the addition of water or a carboxylic acid, e.g., benzoic acid, into any of the component parts of the composition. In one embodiment, the component parts do not contain either a carboxylic acid or added water such that the only water present during the curing reaction is water that may optionally be present at the site of implantation in the body.

In one embodiment, the fully hardened polyurethane or polyureaurethane composition possesses sufficient mechanical properties to be weight bearing, for example for use as a weight-bearing implant in bone, such as a bone void filler, or a bone cement.

In one embodiment, one or more of the components of the composition comprises a prepolymer. A prepolymer is a polymer having reactive end groups, e.g., isocyanate or hydroxyl groups. In one embodiment, the prepolymer comprises an excess of the isocyanate component relative to the polyol/polyamine component. In one embodiment of a two-component composition, one component comprises a prepolymer and no, or substantially no, unreacted polyol; and the second comprises or consists of a hydroxyl terminated prepolymer lacking free isocyanate groups and unreacted polyol or polyamine.

A low molecular weight polymer refers to a polymer having a number average molecular weight in the range of about 500 to 20,000 or 500 to 10,000. A prepolymer containing reactive isocyanate end groups is formed, for example, from the initial reaction of an excess of isocyanate with a limiting amount of polyol or polyamine.

Each of the components may also independently comprise an optional particulate material and an optional chain extender, crosslinker, or curative.

As discussed above, the components of the settable composition are provided as individual units, each containing reagents in amounts such that when the components are mixed together, they form a mixture that fully reacts or cures into a hardened composition after a period of time at room or body temperature. For example, where the settable composition comprises two putties, A and B, putty A comprises an excess of the isocyanate component relative to the polyol component and putty B comprises less of the isocyanate component and more of the polyol/polyamine component than putty A. Putty B also optionally comprises a chain extender and/or crosslinker. Each putty optionally contains an amount of particulate material suspended in the liquid components to form a composition having a putty-like consistency.

In one embodiment, the particulate material is selected from one or more of a polyurethane, calcium sulfate, calcium phosphosilicate, sodium phosphate, calcium aluminate, calcium phosphate, hydroxyapatite, demineralized bone, or mineralized bone. Other particulate materials may also be used, as described infra.

In one embodiment, putty A comprises 15-50% of the isocyanate component, 0.5-5% of the polyol component, and 40-75% particulate material, based upon total weight of putty A; putty B comprises 1-10% of the isocyanate component, 3-15% of the polyol component, and 65-85% particulate material, based upon total weight of putty B.

In one embodiment, putty A comprises 20-35% of the isocyanate component, 0.5-5% of the polyol component, and 50-75% particulate material, based upon total weight of putty A; putty B comprises 1-10% of the isocyanate component, 3-15% of the polyol component, and 75-85% particulate material, based upon total weight of putty B.

The Isocyanate Component

In one embodiment, the isocyanate component comprises or consists of an aromatic isocyanate, an aliphatic isocyanate, a cycloaliphatic isocyanate, or an adduct of an isocyanate, or a mixture of any of the foregoing. A mixture refers to a mixture of two or more of the foregoing. For example, the isocyanate component may comprise or consist of a mixture of two or more isocyanates independently selected from an aromatic isocyanate, an aliphatic isocyanate, a cycloaliphatic isocyanate, and an adduct of an isocyanate.

In one embodiment, the isocyanate is an aliphatic isocyanate selected from the group consisting of ethyl lysine diisocyanate, hexamethylene diisocyanate, cyclohexyl diisocyanate.

In one embodiment, the isocyanate component comprises one or more isocyanates that are relatively non-absorbable. In one embodiment, the isocyanate is an aromatic isocyanate selected from diphenylmethanediisocyanate (MDI), including mixtures thereof such as mixtures of 2,4'-diphenylmethanediisocyanate and 4,4'-diphenylmethanediisocyanate isomers (ISONATE 50 OP, Dow Chemical Co. and RUBINATE 9433, Huntsman Corp.) and its pure 4,4-diphenylmethanediisocyanate form (MONDUR M, Bayer AG and RUBINATE 44, Huntsman Corp.). In one embodiment, the aromatic isocyanate is one of the commercially available polymeric isocyanates ISONATE 143L, ISONATE PAPI 901, and ISONATE PAPI 27 (Dow Chemical Co.). These isocyanates, particularly the diphenylmethane derivatives, generally result in non-absorbable or slowly absorbable polyurethanes.

In one embodiment in which the composition is fully or partially absorbable, the isocyanate component comprises or consists of [5-[2-[2-(4-Isocyanatobenzoyl)oxypropanoyloxy]-ethoxy]-1-methyl-2-oxo-pentyl]-4-isocyanatobenzoate, or "ALD". In one embodiment, the two lactyl moieties of ALD each are racemic. Alternatively, these lactyl moieties may both have D or the L conformations. Alternatively, one lactyl moiety may be D while the other is L, or one may be D, L while the other is D or L. Such changes in stereochemistry may improve the physical and/or biological properties of the resulting polymer.

In one embodiment, the adduct of an isocyanate is selected from a hexamethylene diisocyanate trimer (DESMODUR N-3390) and a hexamethylene diisocyanate biuret (DESMODUR N-100) both commercially available from Bayer AG.

In one embodiment, the settable composition, which may be formed from a polymer selected from a polyurethane, a polyureaurethane, a polyetherurethane, or a polyesterurethane comprises at least one hydrolysable linkage. In one embodiment, the at least one hydrolysable linkage is derived from glycolic acid, lactic acid, caprolactone, or p-dioxanone. In one embodiment, the at least one hydrolysable linkage is selected from the group consisting of ester, amide, anhydride and sulfonamide linkages between the ester-urethane, urethane- or ureaurethane-containing groups. In one embodiment, the composition comprises one or more glycolyl, lactyl, or caprolactyl hydrolysable ester linkages. In one embodiment, the composition comprises one or more ethylene glycol, diethylene glycol, propane diol or butane diol hydrolysable ester linkages. In one embodiment, the composition comprises one or more ethylene diamine, propane diamine, butane diamine, hexamethylene diamine and polyalkylene diamine hydrolysable amide linkages. In one embodiment, the composition comprises one or more lactyl hydrolysable ester linkages and each asymmetric lactyl moiety present in the polymer is selected from one or more of the D, the L or the DL (racemic) stereoisomers.

The hydrolysable isocyanate based compositions are degradable at least due to the presence of functional groups in the polymer chain that are readily hydrolysable under physiological conditions. Thus, the term "partially degradable" as used in the present specification encompasses the percentage of functional groups in the polymer chain that are hydrolyzed compared to the total number of hydrolysable groups. In this context, a partially degradable isocyanate based composition encompasses compositions in which, after a suitable period of time, about 75% of the hydrolysable groups are hydrolyzed. In certain embodiments, a partially degradable compositions is one in which about 25% to 75% or 50% to 75% or about 75% to 90% of the hydrolysable groups are hydrolyzed.

The rate of degradation of the compositions can be controlled in order to provide compositions that degrade at a slower or faster rate, compared to a base composition. In general, the rate of degradation is controlled by varying the isocyanate and polyol/polyamine components of the compositions, as well as the optional chain extender component according to the following parameters. In one aspect, the rate of degradation is controlled by choice of the isocyanate and polyol. Generally, the more hydrolysable linkages, the faster it will degrade while less hydrolysable linkages will degrade slower. In another aspect, the rate of degradation is controlled by varying the hydrophobic/hydrophilic balance of the polyol/polyamine component. Generally, the more carbon atoms or methylene groups between the hydrolysable functions, the slower will be the hydrolysis. For example, ethylene glycol will provide a composition that hydrolyses more rapidly than, for example, 1,3 propane diol, which in turn hydrolyses more rapidly than 1,4 butane diol. In addition, the use of hydrolysable diamines as chain extenders may increase the rate of hydrolysis. In another aspect, copolymers of caprolactone and glycolide hydrolyze faster than copolymers of caprolactone and lactide and the addition of D, L-lactide also increases the rate of hydrolysis. Thus, for example, a bis-diphenyldiisocyanate bridged with a polyglycolide, a polyglycolide-co-lactide, a polylactide, a polycaprolactone-co-glycolide, a polycaprolactone-co-lactide, a polycaprolactone will hydrolyze at increasingly slower rates. For comparison, polyurethanes prepared using methylene bis-diphenyldiisocyanate, with no hydrolyzable linkages, are not significantly degradable under physiological conditions. In other embodiments, enzymatic sensitive sites such as di or polylysines or arginines are incorporated into one or more of the substituents. In another embodiment, the polyol or polyamine component, e.g., hydroxymethylglycolate, may have a hydrolysable linkage to increase the rate of degradation.

In one embodiment, the isocyanate component comprises a polyaromatic di- or polyisocyanate having at least one hydrolysable linkage bridging at least two of the aromatic rings. In certain embodiments, the hydrolysable linkage bridging the aromatic rings is derived from glycolic acid, lactic acid, caprolactone, or p-dioxanone. In most cases, the hydrolyzable linkage is an ester which may degrade into an acid and an alcohol as a result of exposure to water or to naturally occurring esterases. Amide linkages are usually more difficult to hydrolyze than esters. Another option is the easily hydrolyzable acid anhydride linkage. Sulfonamides may also be considered in this context. The polyaromatic di- or polyisocyanates described herein are distinct from isocyantes having only a single aromatic ring such as toluene diisocyante, methylene bis-p-phenyl diisocyanate, and aromatic polyisocyanates generally. Suitable isocyanates are described in U.S. Pat. No. 7,772,352 and U.S. Patent Application Serial No. 2009/0292029, each of which is incorporated herein by reference.

In certain embodiments, the fully cured isocyanate based compositions have a defined pore size. Porosity may be controlled through the inclusion of water, surfactants, and/or cell openers during the process of combining the one or more isocyanate components with the polyol/polyamine component to form the isocyanate based compositions. For example, porosity may be controlled by the addition of a small amount of water to a prepolymer containing isocyanate groups. The water reacts with the isocyanate group to form carbon dioxide, resulting in porosity.

In one embodiment, the solid form has an average pore size in the range of from about 5 to 700 microns. In certain embodiments, the average pore size is from about 5 to 100 microns, from about 5 to 300 microns, from about 5 to 500 microns, and from about 5 to 700 microns. In certain embodiments, the average pore size is from about 100 to 300 microns, from about 200 to 500 microns, from about 300 to 600 microns, and from about 500 to 700 microns, or greater.

In another embodiment, the solid form has an average pore size in the submicron range. In certain embodiments, the average pore size is from about 100 to 1000 nanometers, from about 100 to 400 nanometers, from about 400 to 800 nanometers, from about 200 to 600 nanometers, or from about 500 to 900 nanometers.

Porosity may also be introduced into through the use of porous filler materials (e.g., commercially available calcium phosphates with pore sizes of 200 microns or greater).

In one embodiment, the isocyanate based compositions are formed from an isocyanate component that comprises or consists of a glycolide-linked polyaromatic diisocyanate monomer and a polyol component that comprises or consists of a polycaprolactone-co-glycolide polyol. In one embodiment, the isocyanate based compositions are formed from a reaction that also comprises butanediol, e.g., as a chain extender. In one embodiment, the composition is formed from a reaction that further comprises one or more of water, a carboxylic acid, e.g., benzoic acid (as a foaming agent), a divalent or polyvalent metal salt, a metal carbonate or bicarbonate, or a phosphate, e.g., for osteoconductivity. In one embodiment, the glycolide-linked diisocyanate monomer has the following structure:

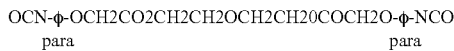

OCN-φ-OCH2CO2CH2CH2OCH2CH2OCOCH2O-φ-NCO
para                                            para In one embodiment, the polycaprolactone-co-glycolide polyol has the following structure:

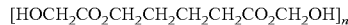

[HOCH$_2$CO$_2$CH$_2$CH$_2$CH$_2$CH$_2$CO$_2$CH$_2$OH]$_n$

In one embodiment, the isocyanate based compositions are formed from an isocyanate component that comprises or consists of a lactide linked diisocyanate monomer and a polyol component that comprises or consists of a polycaprolactone-co-lactide polyol. In one embodiment, the isocyanate based compositions are formed from a reaction that also comprises butanediol, e.g., as a chain extender. In one embodiment, the composition is formed from a reaction that further comprises one or more of water, a carboxylic acid, e.g., benzoic acid (as a foaming agent), a divalent or polyvalent metal salt, a metal carbonate or bicarbonate, or a phosphate, e.g., for osteoconductivity. In one embodiment, the lactide-linked diisocyanate monomer has the following structure:

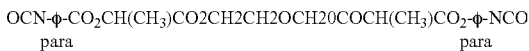

OCN-φ-CO$_2$CH(CH$_3$)CO2CH2CH2OCH2OCOCH(CH$_3$)CO$_2$-φ-NCO
para                                                      para In one embodiment, the polycaprolactone-co-lactide polyol has the following structure:

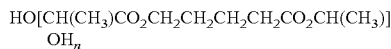

HO[CH(CH$_3$)CO$_2$CH$_2$CH$_2$CH$_2$CH$_2$CO$_2$CH(CH$_3$)]OH$_n$

The Polyol/Polyamine Component

The diols, polyols, and polyamines suitable for use in forming absorbable polyurethane-based compositions are either degradable or non-degradable, or a mixture of the two. As used herein, the term "polyol" is meant to refer generically to diols and polyols, unless indicated otherwise. Generally, absorbable isocyanate based compositions are formed by the combination of an excess of the isocyanate component with the polyol/polyamine component. The relative amounts are calculated as the molar ratio of NCO groups of the isocyanate component (I) to the active hydrogen functional groups (H) (e.g., hydroxyl, amino, and mixtures thereof) of the polyol/polyamine component. Generally, the ratio of polyisocyanate to polyol/polyamine (I:H) is at least 0.5:1. In certain embodiments, the ratio is about 1:1, about 1.5:1, about 2:1, about 3:1, or about 4:1. In other embodiments, the ratio is about 5:1, about 8:1, about 10:1, about 20:1, or about 50:1.

In certain embodiments, the polyol/polyamine component is present in an isocyanate prepolymer in an amount of from about 0.5% to about 50% by weight of the prepolymer. In certain embodiments, the polyol/polyamine component is present in an amount of from about 0.5% to 10%, from about 10% to 20%, from about 20% to 35%, from about 25% to 40%, or from about 35% to 50% by weight of the prepolymer.

Polyols suitable for use include biocompatible, naturally occurring polyols, synthetic polyols, and mixtures thereof. In certain embodiments, the polyols comprise at least one ester group. In certain embodiments, the polyol comprises 2 to 4 ester groups or 5 to 10 ester groups. In one embodiment, the polyol has two or more hydroxyl groups. Suitable polyols include diols and polydiols having repeating units containing up to about 18 carbon atoms. Examples of suitable diols include 1,2-ethanediol (ethylene glycol), 1,2-propanediol (propylene glycol), 1,3-propanediol, 1,4-butanediol, 1,5-pentanediol, 1,3-cyclopentanediol, 1,6-hexanediol, 1,8-octanediol and combinations thereof. Examples of preferred polydiols include polyethylene glycol with molecular weights of from about 500 to about 10000, polytetramethylene ether glycols, polyols derived from glycolide, lactide, trimethylenecarbonate, p-dioxanone and/or caprolactone with molecular weights of about 500 to about 10000.

In one embodiment, one or more alkylpyrrolidones (see e.g., U.S. Pat. No. 7,955,616) may be added to the polyol component to improve healing.

In one embodiment, the polyol is a synthetic polyol selected from a polycaprolactone polyol, polyester polyols, polyadipate polyols (e.g., poly(hexane-adipate) diol, poly (butane-adipate) diol, poly(ethylene/propylene-adipate) diol, poly(hexane/adipate/isophthalate diol)), and polyols that have been derived from a synthetic acid (e.g., isophthalic acid, maleic acid). An example of a suitable biocompatible synthetic polyol is a polycaprolactone diol that is commercially available from Dow Chemical under the trade name TONE 32 B8. a polycaprolactone co-glycolide or a polycaprolactone co-lactide. Further non-limiting examples of suitable synthetic polyols include poly(oxypropylene) glycols, poly(oxytetramethylene) glycols, and poly (oxyethylene) glycols. In one embodiment, the synthetic polyol is selected from a polycaprolactone co-glycolide or a polycaprolactone co-lactide.

In one embodiment, the polyol is a naturally occurring polyol selected from castor oil and lesquerella oil, the polyols that may be obtained by chemical modification of naturally occurring vegetable oils (e.g., castor oil, olive oil, sesame oil, corn oil), naturally occurring oils that have been trans-esterified (e.g., a modified castor oil polyol that has been prepared by the transesterification reaction of natural castor oil with suitable crosslinkers (e.g., glycerol, trimethylolpropane, and the like) or with acids (such as adipic acid), and naturally occurring oils that have been hydrogenated.

Further non-limiting examples of suitable naturally occurring polyols include the commercially available castor-oil-based polyols CASPOL5001, CASPOL1962, and CASPOL5004 (all available from CasChem, Inc.). In certain embodiments, the polyol is not a naturally occurring polyol such as castor oil and lesquerella oil.

In certain embodiments, an isocyanate prepolymer is combined with a polyamine to form a poly(urethane-urea). The polyamine may be a primary or secondary di-amine, or a hindered amine. Non-limiting examples of suitable polyamines include, hindered diamine (e.g., isophorone diamine, "IPDA"), 1,4-cyclohexyl diamine, 1,3-pentane diamine, and aliphatic secondary diamines, and mixtures thereof. In certain embodiments of the present invention, aliphatic diamines and cycloaliphatic diamines may be particularly suitable, and may offer improved biocompatibility. Commercially available examples of suitable polyamines include CLEARLINK 1000 (Dorf Ketal).

Amines including diamines that may be suitable for use in the preparation of polyurea and polyureaurethanes include but are not limited to polyethyleneimines, PEG amines with weight average molecular weights from about 500 to about 5,000, polyoxypropylenediamines available under the tradename JEFFAMINES (Huntsman Corporation, Houston, Tex.) and polyetherdiamines in general, spermine, spermidine, hexamethylenediamine, octamethylenediamine, decamethylenediamine, dodecamethylenediamine, hexadecamethylenediamine, octadecamethylenediamine, polyamidoamine dendrimers, dextrans, PEG-dextran conjugates, cysteines, proteins and peptides containing amines, non-biologically active symmetrical and asymmetrical diamino compounds containing saturated and unsaturated, substituted and unsubstituted alkyl, aryl and alkylaryl groups having from about 2 to about 18 carbon atoms. Further, the diamino compound can be synthesized containing a hydrolyzable link such as one or more ester groups to accelerate the rate of polymer degradation (absorption) in the body. The following structure exemplifies this concept for hexamethylenediamine: $H_2NCH_2CH_2CH_2COOCH_2CH_2NH_2$.

In certain embodiments, the polyol comprises 2 to 4 ester groups or 5 to 10 ester groups. Suitable polyols have at least two hydroxyl groups. In certain embodiments, the polyol has three or more hydroxyl groups making them crosslinkers.

The Chain-Extender/Crosslinker Component

In certain embodiments, one or more optional chain extenders or crosslinkers is incorporated in the formation of the absorbable isocyanate-based compositions. In certain embodiments, only a chain extender is present. In other embodiments, both a chain extender and a crosslinker are present. In one embodiment, the one or more chain extenders is a low molecular weight polyhydroxyl- and/or polyamine-terminated compound having a molecular weight in the range of 10 to 500 Daltons and a functionality of at least two. In certain embodiments, the chain extender is a short-chain diol or diamine. In a particular embodiment, the chain extender or crosslinker is selected from glycerol, 1,4 butanediol, 1,6-hexanediol, diethylene glycol, and combinations thereof. Chain extenders having a functionality of three or more than three are also referred to as crosslinkers. In certain embodiments, the compositions of the invention are formed without crosslinkers and the compositions of the invention are not crosslinked. In other embodiments, the compositions of the invention are formed with one or more crosslinkers. The degree of crosslinking can be controlled, for example, by varying the amount of crosslinker present.

In certain embodiments, the chain-extender or crosslinker is present in an isocyanate prepolymer in an amount in the range of about 5% to about 80% by weight of the isocyanate prepolymer. In certain embodiments, the chain-extender or crosslinker is present in an amount of from about 5% to 20%, about 20% to 30%, about 30% to 40%, about 40% to 50%, about 50% to 60%, from about 60% to 70%, or from about 70% to 80% by weight of the isocyanate prepolymer.

The chain extender may be degradable or non-degradable. Preferably, at least one degradable chain extender is used. Suitable degradable chain extenders for use in the present invention are described in U.S. Patent Application Serial No. 2009/0082540, which is incorporated herein by reference. In one embodiment, the at least one degradable chain extender is $HOCH_2CO_2CH_2CH_2OH$ or $HOCH_2CO_2CH_2CH_2O_2CCH_2OH$.

Other suitable chain-extenders or crosslinkers include natural or synthetic aliphatic polyols. Suitable polydiols for use in the present invention include diol or diol repeating units with up to 8 carbon atoms. Non-limiting examples include 1,2-ethanediol (ethylene glycol), 1,2-propanediol (propylene glycol), 1,3-propanediol, 1,4-butanediol, 1,5-pentanediol, 1,3-cyclopentanediol, 1,6-hexanediol, 1,4-cyclohexanediol, 1,8-octanediol and combinations thereof In other embodiments, the chain extender is a polyol selected from polyethylene glycol and polypropylene glycol having molecular weights of 500-10000 Daltons. Other examples include CASPOL1962 and CASPOL5004. In certain embodiments the preferred polydiols include polydiols selected from polyethylene glycol and polypropylene glycol with molecular weights of 500-10000. In some embodiments, the crosslinker is a non-absorbable crosslinker selected from triethanolamine (TEA), trimethylolpropane, and QUADROL (BASF Corp.). In some embodiments, the chain-extender is a non-degradable chain extender selected from 1,4-butanediol, 1,6-hexanediol, and diethylene glycol. The chain-extender or crosslinker may be present in an isocyanate prepolymer in an amount in the range of about 10% to about 80% by weight of the isocyanate prepolymer.

In another embodiment, the dual putty system is able to set and adhere in aqueous environments. By nature, the isocyanate component, even containing hydrolysable linkages, is essentially hydrophobic and will resist dissolution in aqueous systems. This is true for diamines in this context. It has been found that making the diol more hydrophobic by adding a hydrophobic hydrocarbon-rich residue to a polyol, e.g., glyceryl-1 or 2-monostearate, a more water resistant system is obtained. A variation of this embodiment involves the substitution of a silicon-based moiety for the hydrocarbon-rich residue although this may affect absorbability. Alternatively hydrophobicity and setting rate in aqueous environments can be improved through the use of hydrophobic fillers such as insoluble or weakly soluble aliphatic molecules and salts thereof, including divalent salts, (eg calcium, magnesium, or zinc) of fatty acids. Also useful are cholesterol and its derivatives, as well as silated derivatives of ceramics or bone (Shimp et al., 7,270,813) Another embodiment of a water resistant, settable, dual putty system adds a small amount of hydrophobic isocyanate to the relatively hydrophilic polyol component resulting in a water-resistant mixture of polyol containing a minor amount of hydrophobic polyurethane prepolymer. In one embodiment, the chain extender does not comprise an amino acid group.

Water

In certain embodiments, the compositions of the invention contain no added water. In some embodiments, the compositions are anhydrous. In certain embodiments where there is no added water, water may nevertheless be present in small amounts. For example, certain commercially-available polyols comprise a mixture of the polyol and a small amount of water. In addition, certain optional particulate materials as described herein, such as calcium carbonate may comprise bound water. Formulating the compositions in an atmosphere that contains moisture may also result in the incorporation of water into the compositions. In certain embodiments of the present invention, the compositions are prepared under a nitrogen purge that comprises a desired amount of moisture, thereby controlling the water content of the compositions. In other embodiments, water may be added to the compositions during the process of their formation from the component parts. In other embodiments, the compositions are prepared under essentially water-free conditions with anhydrous components such that the resulting compositions are essentially anhydrous.

In certain embodiments, water is present in the compositions being made in an amount from at least about 0.01% to about 3% by weight of the composition. In certain embodiments, water is present in an amount of from about 0.05% to 1%, from about 0.05% to 1.5%, from about 0.1% to 1%, from about 0.1% to 1.5%, from about 0.1% to 2%, from about 1% to 2%, or from about 2% to 3%.

Particulate Materials

The settable compositions of the invention may contain optional particulate materials. In one embodiment, the particulate material is an osteoconductive material. In certain embodiments, the particulate material supports or promotes the growth of bone at the application site. In one embodiment, the particulate material is non-resorbable. In certain embodiments, the mean particle size of the optional particulate material is in the micron or submicron range. In one embodiment, the mean particle size is from about 0.001 to 0.100 microns, from about 0.100 to 5 microns, from about 5 to 100 microns, from about 5 to 500 microns, or from about 500 to 2000 microns.

In one embodiment, the optional particulate material is a carbonate or bicarbonate material. In one embodiment, the carbonate or bicarbonate material comprises or consists of one or more of calcium carbonate, magnesium carbonate, aluminum carbonate, iron carbonate, zinc carbonate, calcium bicarbonate, and sodium bicarbonate. In one embodiment, the optional particulate material comprises or consists of bone (e.g., demineralized bone, bone morphogenetic protein, allograft bone, and/or autogenous bone), calcium phosphate, siliconized calcium phosphate, substituted calcium phosphates (e.g., with magnesium, strontium, or silicate), calcium pyrophosphate, hydroxyapatite, polymethyl methacrylate, glass-ionomer, absorbable phosphate glass, calcium sulfate, tricalcium phosphate (e.g., beta tricalcium phosphate), or any combination of the foregoing. Other examples include one or more poly ether ether ketones (e.g., PEEK), REPLACE (Cortek, Inc.), EXPANCEL (Akzo Nobel). In other embodiments, the particulate material is a ceramic such as substituted calcium phosphates (e.g, silicate, strontium or magnesium substitution) or a glass such as bioglass. In one embodiment, the particulate material comprises or consists of one or more of calcium sulfate, calcium phosphosilicate, sodium phosphate, calcium aluminate, calcium phosphate, hydroxyapatite, demineralized bone, or mineralized bone.

The optional particulate material, when present, may comprise any one or more of the materials listed in the embodiments above. In one embodiment, the particulate material, if present in the composition, does not comprise calcium carbonate. In one embodiment, the particulate material may be polymeric such as a polyurethane.

In one embodiment, the particulate material is present in an amount of from about 0.01% to about 10% by weight of the composition. In certain embodiments, the optional particulate material is present in an amount of 0.10% to 10%, 1% to 10%, or 5% to 10%. In other embodiments, the optional particulate material is present in an amount of from about 10% to about 20% by weight of the composition, or from about 20% to 30%, about 30% to 40%, about 40% to 50%, about 50% to 60%, about 60% to 70% or about 70% to 80% by weight of the composition.

In one embodiment, the particulate additive material is graphene (available from Applied Graphene Materials and Thomas Swan, Ltd.), a single atomic layer of graphite that is electrically conductive, highly elastic, is about 100 times stronger than steel and which may be of value improving the quality of tissue healing and new bone stimulation.

Other Optional Additives

The compositions of the invention may also optionally comprise one or more "cell openers." Non-limiting examples include ORTOGEL501 (Goldschmidt) and X-AIR (Specialty Polymers & Services). In certain embodiments, the cell openers are present in an amount in of from about 0.1% to 5% by weight of the composition. In one embodiment, the cell openers are present in an amount in of from about 1% to 2% or 1% to 3% by weight of the composition. Optional additives can be added to the magnesium based section but for the malonate/cyanoacrylate section, no active hydrogen atoms can be present including those in water because they will initiate polymerization.

The compositions of the invention may also optionally comprise one or more therapeutic agents. In one embodiment, the one or more therapeutic agents are selected from an anti-cancer agent, an antimicrobial agent, an antibiotic, a local anesthetic or analgesic, a statin and an anti-inflammatory agent. In one embodiment, the antibiotic is selected from a broad spectrum antibiotic, such as gentamicin, clindamycin, and erythromycin, or a gram positive and gram negative family antibiotic such as an ampicillin and a cephalosporin. In one embodiment, the local anesthetic or analgesic is selected from lidocaine, bupivacaine, tetracaine, and ropivacaine. In one embodiment, the local anesthetic or analgesic is selected from lidocaine, benzocaine and fentanyl (a potent non-opioid anesthetic). In one embodiment, the one or more anti-inflammatory substances is selected from a non-specific anti-inflammatory such as ibuprofen and aspirin, or a COX-2 specific inhibitor such as rofecoxib and celeboxib.

In one embodiment, component A is a putty comprised of a concentrated aqueous solution of a polyanionic polymer, e.g., carboxymethylcellulose, and component B is a putty comprised of a concentrated aqueous solution of a polycationic polymer. e.g., chitosan, either of which may be optionally crosslinked. The combined materials are hemostatic when applied to a bleeding surface.

In one embodiment, the compositions further comprise one or more of an antioxidant, a colorant, a steroid, calcium stearate, tocopheryl acetate, and triacetin. In one embodiment, the antioxidant is selected from IRGANOX 1010 and IRGANOX 1035 (Ciba Geigy), and CYANOX 1790 and CYANOX 2777 (Cytec Industries). In certain embodiments, the antioxidant is present in an amount of from about 0.01% to 0.5% by weight of the composition. In one embodiment, the composition comprises one or more of calcium stearate, tocopheryl acetate, and triacetin, each present in a component putty of the composition in an amount ranging from 0.1 to 5% based upon the weight of the component putty. Non-limiting examples of colorants that may be included in the compositions are gentian violet, D&C Violet #2, and D&C Green #6.

In one embodiment, the steroid is a steroid-based compound, such as an intracellular messenger, effective to modulate the rate of tissue growth, including bone growth.

In one embodiment, the compositions further comprise one or more growth factors, for example BMP-2, BMP-7, PDGF, EGF, etc.

EQUIVALENTS

Those skilled in the art will recognize or be able to ascertain using no more than routine experimentation, many equivalents to the specific embodiments of the invention described herein. Such equivalents are intended to be encompassed by the following claims.

All references cited herein are incorporated herein by reference in their entirety and for all purposes to the same extent as if each individual publication or patent or patent application was specifically and individually indicated to be incorporated by reference in its entirety for all purposes.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

What is claimed is:

1. A package comprising one or a plurality of settable compositions, each composition consisting of a set of two reactive putties, A and B, the putties of the set each comprising amounts of reagents which, upon mixing together, react and cure into a final hardened form selected from the group consisting of a polyurethane, a polyureaurethane, a polyetherurethane, and a polyesterurethane, over a period of time at room or body temperature, each putty being physically separated from the other putty of its set within the package, and optionally, from other sets of putties, wherein putty A comprises 15-40% of an isocyanate component, 0.5-5% of a polyol or polyamine component, and 50-75% particulate material, based upon total weight of putty A; and putty B comprises 1-10% of the isocyanate component, 3-15% of the polyol or polyamine component, and 75-95% of the particulate material, based upon total weight of putty B.

2. The package of claim 1, wherein the putties are sterile.

3. The package of claim 1, wherein the putties are sterile, the package comprises a plurality of settable compositions, and the package is adapted to permit the removal of one set of putties at a time while leaving the remaining sets in their sealed, sterile, environments.

4. The package of claim 3, wherein the package comprises peelable films configured to allow the exposure of one set of putties at a time.

5. The package of claim 4, wherein each putty is physically separated from the other putty of its set within the package by means of a compartment or plurality of compartments in the package.

6. The package of claim 5, wherein the plurality of compartments comprise depressions or wells.

7. The package of claim 5, wherein the compartments of a set are flexible and separated by at least one breakable seal adapted to allow the putties of the set to be mixed together when the seal is broken.

8. The package of claim 5, wherein the compartments are in the form of one or more syringes.

9. The package of claim 8, wherein the compartments are in the form of a single syringe adapted to maintain individual putties of a set separated from each other within the single syringe.

10. The package of claim 8, wherein the compartments are in the form of a plurality of syringes and each syringe contains a single putty of a set of putties.

11. The package of claim 8, wherein the one or more syringes containing a reactive putty are connected to permit manual, or power-assisted component mixing during or before extrusion or dispensing.

12. The package of claim 1, wherein each compartment comprises one or more surfaces in contact with an individual putty, the one or more surfaces comprising or consisting of a material selected from the group consisting of polytetrafluoroethylene (PTFE), silicone, polypropylene, polyethylene, and polystyrene.

13. The package of claim 1, further comprising a sealed outer envelope completely surrounding the package, and a desiccant.

14. The package of claim 13, wherein the outer envelope is heat sealed.

15. The package of claim 1, wherein the particulate component is selected from one or more of calcium sulfate, calcium phosphosilicate, sodium phosphate, calcium aluminate, calcium phosphate, hydroxyapatite, biomimetic carbonate apatite, demineralized bone, or mineralized bone.

16. The package of claim 1, wherein the particulate component is selected from one or more of a polyaryletherketone-based material, a polymethylmethacrylate-based material, and a non-resorbable metallic filler.

17. The package of claim 1, wherein the package comprises from 1-10 settable compositions.

18. The package of claim 17, wherein the package comprises 1 settable composition.

19. The package of claim 17, wherein the package comprises 2, 4, 6, or 8 settable compositions.

20. The package of claim 17, wherein the individual reactive putties are sterile.

21. The package of claim 17, wherein the individual reactive putties are sterile and the package is adapted to permit the removal of one set of putties at a time while leaving the remaining sets of putties in their sealed, sterile, environments.

22. The package of claim 21, wherein the package comprises an upper peelable film configured to allow the exposure of one set of putties at a time.

23. The package of claim 21, wherein each individual reactive putty is physically separated from the other putty of its set within the package by means of a compartment or plurality of compartments for each set of putties in the package.

24. The package of claim 23, wherein the plurality of compartments comprises depressions or wells.

25. The package of claim 23, wherein the compartments of a set are flexible and separated by at least one breakable seal adapted to allow the individual reactive putties of a set to be mixed together when the seal is broken.

26. The package of claim 23, wherein the compartment or plurality of compartments is in the form of one or a plurality of syringes.

27. The package of claim 26, wherein the one or plurality of syringes is adapted to maintain the individual reactive putties of a set separate from each other within a single syringe.

28. The package of claim 23, wherein each compartment comprises one or more surfaces in contact with an individual reactive putty, the one or more surfaces comprising or consisting of a material selected from the group consisting of polytetrafluoroethylene (PTFE), silicone, polypropylene, polyethylene, and polystyrene.

29. The package of claim 19, further comprising an outer envelope completely surrounding the package, and a desiccant.

30. The package of claim 29, wherein the outer envelope is heat sealed.

31. The package of claim 19, wherein the particulate component is selected from one or more of calcium sulfate, calcium phosphosilicate, sodium phosphate, calcium aluminate, calcium phosphate, hydroxyapatite, biomimetic carbonate apatite, demineralized bone, or mineralized bone.

32. The package of claim 19, wherein the particulate component is selected from one or more of a polyaryletherketone-based material, a polymethylmethacrylate-based material, and a non-resorbable metallic filler.

33. The package of claim 19, wherein each putty of the set comprises a different colorant or dye such that when the component parts of the set are combined to form the settable composition, the different colors mix to form a new color, which new color is also indicative that the composition has been mixed to homogeneity.

34. The package of claim 1, wherein each putty of the set comprises a different colorant or dye such that when the component parts of the set are combined to form the settable composition, the different colors mix to form a new color, which new color is also indicative that the composition has been mixed to homogeneity.

35. The package of claim 1, wherein the polyol or polyamine component comprises one or more different diols, polyols, and polyamines, and mixtures thereof.

36. The package of claim 1, wherein the polyol or polyamine in putty A is present in a prepolymer with the isocyanate component such that there is no unreacted polyol in putty A and the isocyanate component in Putty B is present in a prepolymer such that there is no unreacted isocyanate in putty B.

37. A package comprising one or a plurality of settable compositions, each composition consisting of a set of two individual reactive putties, A and B, the putties of the set each comprising amounts of reagents which, upon mixing together, react and cure into a final hardened form over a period of time at room or body temperature, each putty being physically separated from the other putty of its set within the package, and optionally, from other sets of putties, by means of a compartment or plurality of compartments in the package, wherein the compartments of a set are flexible and separated by at least one breakable seal adapted to allow the individual reactive putties of the set to be mixed together when the seal is broken, wherein putty A comprises 15-40% of an isocyanate component, 0.5-5% of a polyol or polyamine component, and 50-75% of a particulate material, based upon total weight of putty A; and putty B comprises 1-10% of the isocyanate component, 3-15% of the polyol or polyamine component, and 75-95% of the particulate material, based upon total weight of putty B.

38. The package of claim 37, wherein each putty of the set comprises a different colorant or dye such that when the component parts of the set are combined to form the settable composition, the different colors mix to form a new color, which new color is also indicative that the composition has been mixed to homogeneity.

39. The package of claim 37, wherein the polyol or polyamine component comprises one or more different diols, polyols, and polyamines, and mixtures thereof.

40. The package of claim 37, wherein the polyol or polyamine in putty A is present in a prepolymer with the isocyanate component such that there is no unreacted polyol in putty A and the isocyanate component in Putty B is present in a prepolymer such that there is no unreacted isocyanate in putty B.

\* \* \* \* \*